(12) United States Patent
Nalagatla et al.

(10) Patent No.: US 12,059,151 B2
(45) Date of Patent: *Aug. 13, 2024

(54) KNIFE FOR SURGICAL STAPLER AND ASSOCIATED METHOD OF MANUFACTURE WITH MIM AND HIP

(71) Applicant: Cilag GmbH International, Zug (CH)

(72) Inventors: Anil K. Nalagatla, Mason, OH (US); Frederick E. Shelton, IV, Hillsboro, OH (US); Chester O. Baxter, III, Loveland, OH (US); Jerome R. Morgan, Cincinnati, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 91 days.

This patent is subject to a terminal disclaimer.

(21) Appl. No.: 17/155,808

(22) Filed: Jan. 22, 2021

(65) Prior Publication Data

US 2021/0204939 A1 Jul. 8, 2021

Related U.S. Application Data

(63) Continuation of application No. 16/236,676, filed on Dec. 31, 2018, now Pat. No. 11,103,245.

(51) Int. Cl.
*A61B 17/00* (2006.01)
*A61B 17/072* (2006.01)
*B21K 11/02* (2006.01)

(52) U.S. Cl.
CPC ........... *A61B 17/072* (2013.01); *B21K 11/02* (2013.01); *A61B 2017/00526* (2013.01);
(Continued)

(58) Field of Classification Search
CPC ........ A61B 17/072; A61B 2017/00526; A61B 2017/07257; A61B 2017/07264;
(Continued)

(56) References Cited

U.S. PATENT DOCUMENTS 2,859,936 A * 11/1958 Warnken ................. F01D 5/282
  273/DIG. 7
3,031,753 A *  5/1962 Pocoski ............... A45D 29/023
  30/28

(Continued)

FOREIGN PATENT DOCUMENTS

EP     0589454 A2    3/1994
EP     3241506 A1   11/2017
(Continued)

OTHER PUBLICATIONS

European Search Report, Partial, and Provisional Written Opinion dated Mar. 12, 2020, for Application No. 19220044.2, 12 pages.
(Continued)

*Primary Examiner* — Robert F Long
(74) *Attorney, Agent, or Firm* — Frost Brown Todd LLP

(57) ABSTRACT

A method is used to manufacture a knife of an end effector of a surgical instrument. The method includes forming the knife using metal injection molding. The knife has at least one feature having a molded shape. The method also includes machining the at least one feature of the knife to have a machined shape without machining the entire knife. The method also includes incorporating the knife into the end effector of the surgical instrument.

20 Claims, 14 Drawing Sheets

(52) U.S. Cl.
CPC ............ *A61B 2017/07257* (2013.01); *A61B 2017/07264* (2013.01); *A61B 2017/07271* (2013.01); *A61B 2017/07278* (2013.01); *A61B 2017/07285* (2013.01)

(58) Field of Classification Search
CPC ........... A61B 2017/07271; A61B 2017/07278; A61B 2017/07285; A61B 2017/00845; A61B 2017/2927; A61B 17/07207; B21K 11/02
USPC ........................................ 227/175.1–182.1
See application file for complete search history.

(56) References Cited

U.S. PATENT DOCUMENTS

| | | | |
|---|---|---|---|
| 3,946,769 A * | 3/1976 | Caveney | B65B 13/027 |
| | | | 140/93.2 |
| 4,001,366 A * | 1/1977 | Brumlik | A44B 18/0061 |
| | | | 264/145 |
| 4,175,883 A * | 11/1979 | Lemelson | E04H 17/1465 |
| | | | 256/65.14 |
| 4,250,620 A * | 2/1981 | Nishikawa | B26B 13/02 |
| | | | D8/57 |
| 4,706,866 A | 11/1987 | Ebihara | |
| 4,813,143 A | 3/1989 | Scheminger et al. | |
| 4,991,764 A * | 2/1991 | Mericle | A61B 17/07207 |
| | | | 227/19 |
| 5,163,945 A | 11/1992 | Ortiz et al. | |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,297,746 A | 3/1994 | McBride et al. | |
| 5,308,576 A * | 5/1994 | Green | A61B 17/07207 |
| | | | 419/36 |
| 5,333,773 A | 8/1994 | Main et al. | |
| 5,342,373 A | 8/1994 | Stefanchik et al. | |
| 5,350,104 A | 9/1994 | Main et al. | |
| 5,364,001 A | 11/1994 | Bryan | |
| 5,383,895 A * | 1/1995 | Holmes | A61B 17/2909 |
| | | | 606/206 |
| 5,392,487 A * | 2/1995 | Yang | B60S 1/4003 |
| | | | 15/250.32 |
| 5,403,312 A | 4/1995 | Yates et al. | |
| 5,426,857 A * | 6/1995 | Linden | B29C 45/14467 |
| | | | 30/262 |
| 5,431,322 A * | 7/1995 | Green | A61B 17/07207 |
| | | | 227/176.1 |
| 5,431,668 A | 7/1995 | Burbank, III et al. | |
| 5,445,167 A | 8/1995 | Yoon et al. | |
| 5,487,499 A | 1/1996 | Sorrentino et al. | |
| 5,533,661 A | 7/1996 | Main et al. | |
| 5,584,845 A * | 12/1996 | Hart | A61B 17/3201 |
| | | | 606/174 |
| 5,601,573 A | 2/1997 | Fogelberg et al. | |
| 5,636,443 A * | 6/1997 | Linden | B26B 13/28 |
| | | | 30/124 |
| 5,722,306 A | 3/1998 | Vela et al. | |
| 5,807,338 A | 9/1998 | Smith et al. | |
| 5,951,574 A | 9/1999 | Stefanchik et al. | |
| 6,145,418 A * | 11/2000 | Bares | B25B 27/146 |
| | | | 81/421 |
| 6,176,021 B1 | 1/2001 | Sato et al. | |
| 6,185,771 B1 * | 2/2001 | Trusty, Sr. | B25F 1/003 |
| | | | 30/162 |
| 6,269,714 B1 | 8/2001 | Sakai | |
| 6,319,266 B1 | 11/2001 | Stellon et al. | |
| 6,504,114 B1 * | 1/2003 | Lockery | G01G 3/1412 |
| | | | 177/229 |
| 6,959,851 B2 | 11/2005 | Heinrich | |
| 6,988,650 B2 | 1/2006 | Schwemberger et al. | |
| 7,000,818 B2 | 2/2006 | Shelton, IV et al. | |
| 7,043,819 B1 | 5/2006 | Arnold | |
| 7,134,587 B2 | 11/2006 | Schwemberger et al. | |
| 7,147,140 B2 | 12/2006 | Wukusick et al. | |
| 7,195,631 B2 | 3/2007 | Dumbauld | |
| 7,204,404 B2 | 4/2007 | Nguyen et al. | |
| 7,207,472 B2 | 4/2007 | Wukusick et al. | |
| 7,261,724 B2 | 8/2007 | Molitor et al. | |
| 7,276,068 B2 * | 10/2007 | Johnson | A61B 18/1442 |
| | | | 606/45 |
| 7,380,696 B2 | 6/2008 | Shelton, IV et al. | |
| 7,422,139 B2 | 9/2008 | Shelton, IV et al. | |
| 7,464,849 B2 | 12/2008 | Shelton, IV et al. | |
| 7,670,334 B2 | 3/2010 | Hueil et al. | |
| 7,686,820 B2 | 3/2010 | Huitema et al. | |
| 7,699,860 B2 | 4/2010 | Huitema et al. | |
| 7,731,724 B2 | 6/2010 | Huitema et al. | |
| 7,753,245 B2 | 7/2010 | Boudreaux et al. | |
| 7,771,425 B2 | 8/2010 | Dycus et al. | |
| 7,845,537 B2 | 12/2010 | Shelton, IV et al. | |
| 7,980,443 B2 | 7/2011 | Scheib et al. | |
| 8,021,389 B2 | 9/2011 | Molz, IV | |
| 8,038,686 B2 | 10/2011 | Huitema et al. | |
| 8,087,562 B1 | 1/2012 | Manoux et al. | |
| 8,210,411 B2 | 7/2012 | Yates et al. | |
| 8,220,688 B2 | 7/2012 | Laurent et al. | |
| 8,262,679 B2 | 9/2012 | Nguyen | |
| 8,308,040 B2 | 11/2012 | Huang et al. | |
| 8,393,514 B2 | 3/2013 | Shelton, IV et al. | |
| 8,408,439 B2 | 4/2013 | Huang et al. | |
| 8,453,914 B2 | 6/2013 | Laurent et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 8,770,458 B2 | 7/2014 | Scirica | |
| 8,910,847 B2 | 12/2014 | Nalagatla et al. | |
| 9,072,535 B2 | 7/2015 | Shelton, IV et al. | |
| 9,101,358 B2 | 8/2015 | Kerr et al. | |
| 9,186,142 B2 | 11/2015 | Fanelli et al. | |
| 9,192,383 B2 | 11/2015 | Milliman | |
| 9,345,481 B2 | 5/2016 | Hall et al. | |
| 9,517,065 B2 | 12/2016 | Simms et al. | |
| 9,713,469 B2 | 7/2017 | Leimbach et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 9,907,552 B2 | 3/2018 | Measamer et al. | |
| 9,936,949 B2 | 4/2018 | Measamer et al. | |
| 10,092,292 B2 | 10/2018 | Boudreaux et al. | |
| 10,488,281 B2 * | 11/2019 | Burrow | G01L 5/1627 |
| 11,103,245 B2 | 8/2021 | Nalagatla et al. | |
| 11,330,920 B1 * | 5/2022 | Rogers | A47B 95/04 |
| 2001/0010100 A1 * | 8/2001 | Berg | B25F 1/04 |
| | | | 7/128 |
| 2005/0004568 A1 | 1/2005 | Lawes et al. | |
| 2005/0087521 A1 * | 4/2005 | Yang | B29C 33/3842 |
| | | | 219/121.69 |
| 2005/0139636 A1 | 6/2005 | Schwemberger et al. | |
| 2005/0143759 A1 | 6/2005 | Kelly | |
| 2005/0145672 A1 | 7/2005 | Schwemberger et al. | |
| 2005/0149087 A1 | 7/2005 | Ahlberg et al. | |
| 2006/0047309 A1 | 3/2006 | Cichocki | |
| 2006/0090603 A1 * | 5/2006 | Lewis | B23P 15/40 |
| | | | 76/56 |
| 2006/0219752 A1 | 10/2006 | Arad et al. | |
| 2007/0056932 A1 | 3/2007 | Whitman et al. | |
| 2007/0082229 A1 | 4/2007 | Mirchandani et al. | |
| 2007/0125894 A1 * | 6/2007 | Koop | B01F 27/0724 |
| | | | 241/92 |
| 2007/0169605 A1 | 7/2007 | Szymanski | |
| 2007/0175955 A1 | 8/2007 | Shelton, IV et al. | |
| 2007/0289252 A1 * | 12/2007 | Pinto | A22C 11/125 |
| | | | 53/138.4 |
| 2008/0035701 A1 * | 2/2008 | Racenet | A61B 17/07207 |
| | | | 227/176.1 |
| 2008/0078800 A1 | 4/2008 | Hess et al. | |
| 2008/0142187 A1 | 6/2008 | Jadeed et al. | |
| 2008/0308605 A1 | 12/2008 | Scirica | |
| 2009/0001128 A1 | 1/2009 | Weisenburgh, II et al. | |

(56) References Cited

U.S. PATENT DOCUMENTS

| | | |
|---|---|---|
| 2009/0065552 A1* | 3/2009 | Knodel ............... A61B 17/115 227/180.1 |
| 2010/0127039 A1 | 5/2010 | Hessler |
| 2010/0213240 A1* | 8/2010 | Kostrzewski ...... A61B 17/3209 227/180.1 |
| 2010/0218387 A1 | 9/2010 | Moons ..................... B26B 5/00 30/353 |
| 2010/0249807 A1 | 9/2010 | Chen et al. |
| 2011/0068147 A1 | 3/2011 | Racenet et al. |
| 2011/0207563 A1* | 8/2011 | Anderson ................ F42B 6/04 264/263 |
| 2012/0080498 A1* | 4/2012 | Shelton, IV ......... A61B 17/072 227/180.1 |
| 2012/0116422 A1 | 5/2012 | Triplett et al. |
| 2012/0241496 A1* | 9/2012 | Mandakolathur Vasudevan ......... A61B 17/0684 227/176.1 |
| 2012/0292372 A1 | 11/2012 | Nalagatla et al. |
| 2013/0105545 A1* | 5/2013 | Burbank .......... A61B 17/07207 227/175.1 |
| 2013/0172929 A1* | 7/2013 | Hess ................. A61B 17/1155 227/175.1 |
| 2013/0256382 A1 | 10/2013 | Swayze et al. |
| 2014/0001231 A1* | 1/2014 | Shelton, IV ........... A61B 34/71 227/175.3 |
| 2014/0183244 A1* | 7/2014 | Duque ................. A61B 17/068 606/167 |
| 2014/0239037 A1 | 8/2014 | Boudreaux et al. |
| 2014/0263552 A1 | 9/2014 | Hall et al. |
| 2014/0291378 A1* | 10/2014 | Shelton, IV ..... A61B 17/07207 227/175.2 |
| 2014/0364851 A1* | 12/2014 | Batross .............. A61B 18/1445 606/45 |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2016/0296231 A1* | 10/2016 | Wang .................. A61B 17/068 |
| 2016/0333918 A1* | 11/2016 | Neal ...................... B21J 15/022 |
| 2016/0374672 A1 | 12/2016 | Bear et al. |
| 2017/0027571 A1 | 2/2017 | Nalagatla et al. |
| 2017/0258471 A1 | 9/2017 | DiNardo et al. |
| 2017/0265867 A1 | 9/2017 | Nativ et al. |
| 2018/0042637 A1* | 2/2018 | Craig .................... G10K 11/22 |
| 2018/0056095 A1 | 3/2018 | Messerly et al. |
| 2018/0085932 A1 | 3/2018 | Yu Chen |
| 2018/0132849 A1 | 5/2018 | Miller et al. |
| 2018/0132853 A1 | 5/2018 | Miller et al. |
| 2018/0168610 A1* | 6/2018 | Shelton, IV ....... A61B 17/2816 |
| 2018/0168649 A1* | 6/2018 | Shelton, IV ..... A61B 17/07292 |
| 2018/0310938 A1 | 11/2018 | Kluener et al. |
| 2018/0310939 A1 | 11/2018 | Stager et al. |
| 2018/0368839 A1 | 12/2018 | Shelton, IV et al. |
| 2018/0368840 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2019/0046193 A1 | 2/2019 | Dunki-Jacobs et al. |
| 2019/0083094 A1* | 3/2019 | Racenet ............... A61B 17/105 |
| 2019/0216561 A1* | 7/2019 | Manzo ............ A61B 17/00234 |
| 2019/0254679 A1 | 8/2019 | Russell |
| 2019/0298350 A1* | 10/2019 | Shelton, IV ..... A61B 17/07207 |
| 2019/0298351 A1* | 10/2019 | Shelton, IV ..... A61B 17/07207 |
| 2019/0341753 A1 | 11/2019 | Nemoto et al. |
| 2020/0205812 A1* | 7/2020 | Nalagatla ............... B21K 11/02 |
| 2020/0205815 A1 | 7/2020 | Nalagatla et al. |
| 2020/0205816 A1* | 7/2020 | Nalagatla ............ A61B 17/072 |
| 2020/0206805 A1 | 7/2020 | Nalagatla et al. |
| 2021/0196351 A1* | 7/2021 | Sarley ................ A61B 18/1206 |
| 2021/0204940 A1 | 7/2021 | Nalagatla et al. |
| 2022/0218335 A1* | 7/2022 | Baxter, III .......... A61B 17/072 |
| 2022/0346793 A1* | 11/2022 | Shelton, IV ......... A61B 17/064 |
| 2023/0047701 A1* | 2/2023 | Zhang ................. A61B 17/072 |

FOREIGN PATENT DOCUMENTS

| | | | |
|---|---|---|---|
| EP | 3323358 A1 | 5/2018 | |
| EP | 3420960 A1 * | 1/2019 | ....... A61B 17/07207 |
| JP | 2007-525285 A | 9/2007 | |
| JP | 2008-173424 A | 7/2008 | |
| JP | 2013-517891 A | 5/2013 | |
| WO | WO-2018067451 A1 * | 4/2018 | ....... A61B 17/00234 |
| WO | WO-2021088204 A1 * | 5/2021 | ....... A61B 17/07207 |

OTHER PUBLICATIONS

European Search Report, Extended, and Written Opinion dated Jul. 15, 2020, for Application No. 19220044.2, 14 pages.
International Search Report and Written Opinion dated Jun. 15, 2020, for International Application No. PCT/IB2019/060817, 18 pages.
U.S. Non-Provisional Pat. U.S. Appl. No. 17/155,824
U.S. Pat. No. 11,103,245.
Brazilian Examination Report dated Jul. 5, 2023 for Application No. BR 112021012562-0, 4 pgs.
Indian Examination Report dated Nov. 15, 2022 for Application No. IN 202117027712, 6 pgs.
Japanese Office Action, Notice of Reasons for Refusal, dated Sep. 26, 2023 for Application No. JP 2021-538247, 7 pgs.
Japanese Search Report by Registered Search Organization, dated Sep. 22, 2023 for Application No. JP 2021-538247, 20 pgs.

* cited by examiner

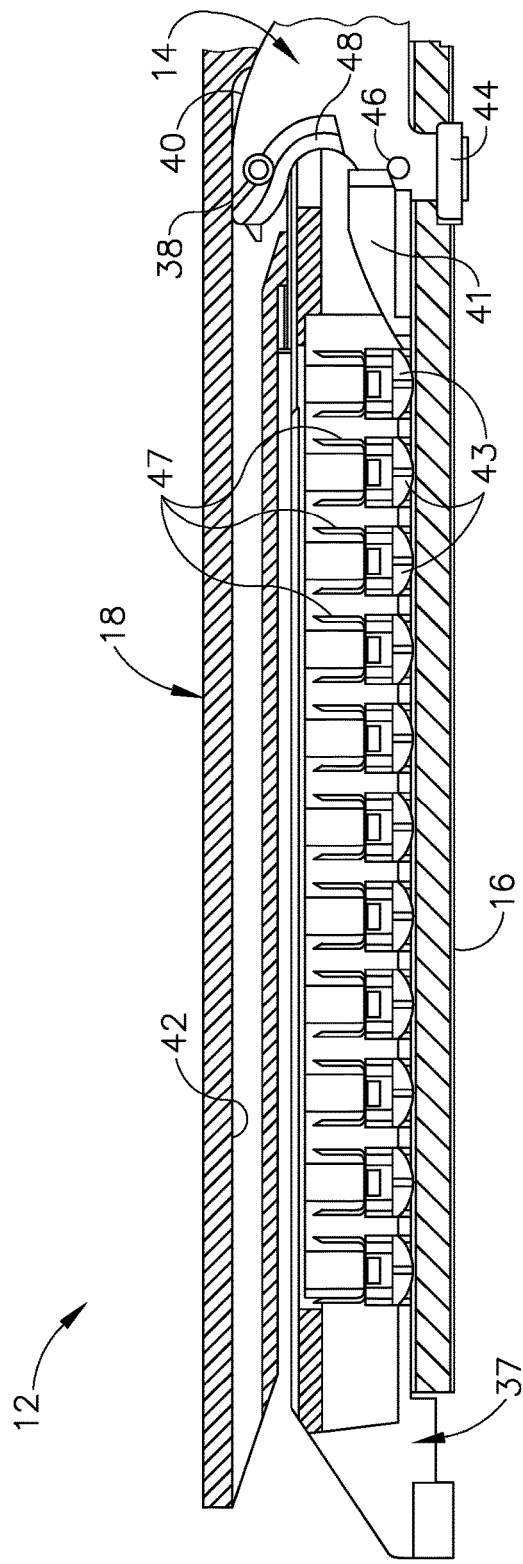
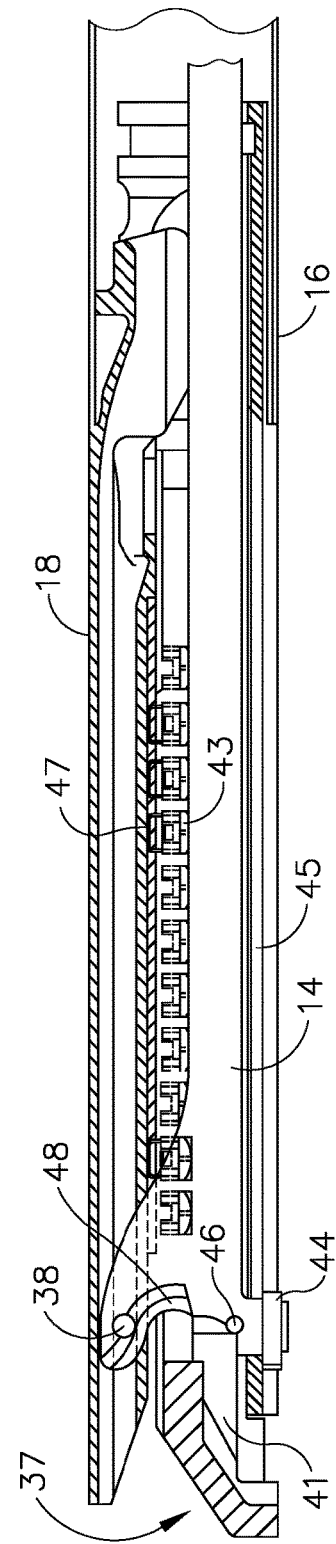
FIG. 4A
FIG. 4B

KNIFE FOR SURGICAL STAPLER AND ASSOCIATED METHOD OF MANUFACTURE WITH MIM AND HIP

This application is a continuation application of U.S. patent application Ser. No. 16/236,676, entitled "Knife for Surgical Stapler and Associated Method of Manufacture with MIM and HIP," filed Dec. 31, 2018, issued as U.S. Pat. No. 11,103,245 on Aug. 31, 2021.

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with the firing beam in a proximal position;

FIG. 4B depicts a side cross-sectional view of the end effector of FIG. 3, taken along line 4-4 of FIG. 3, with the firing beam in a distal position;

Figure 1:
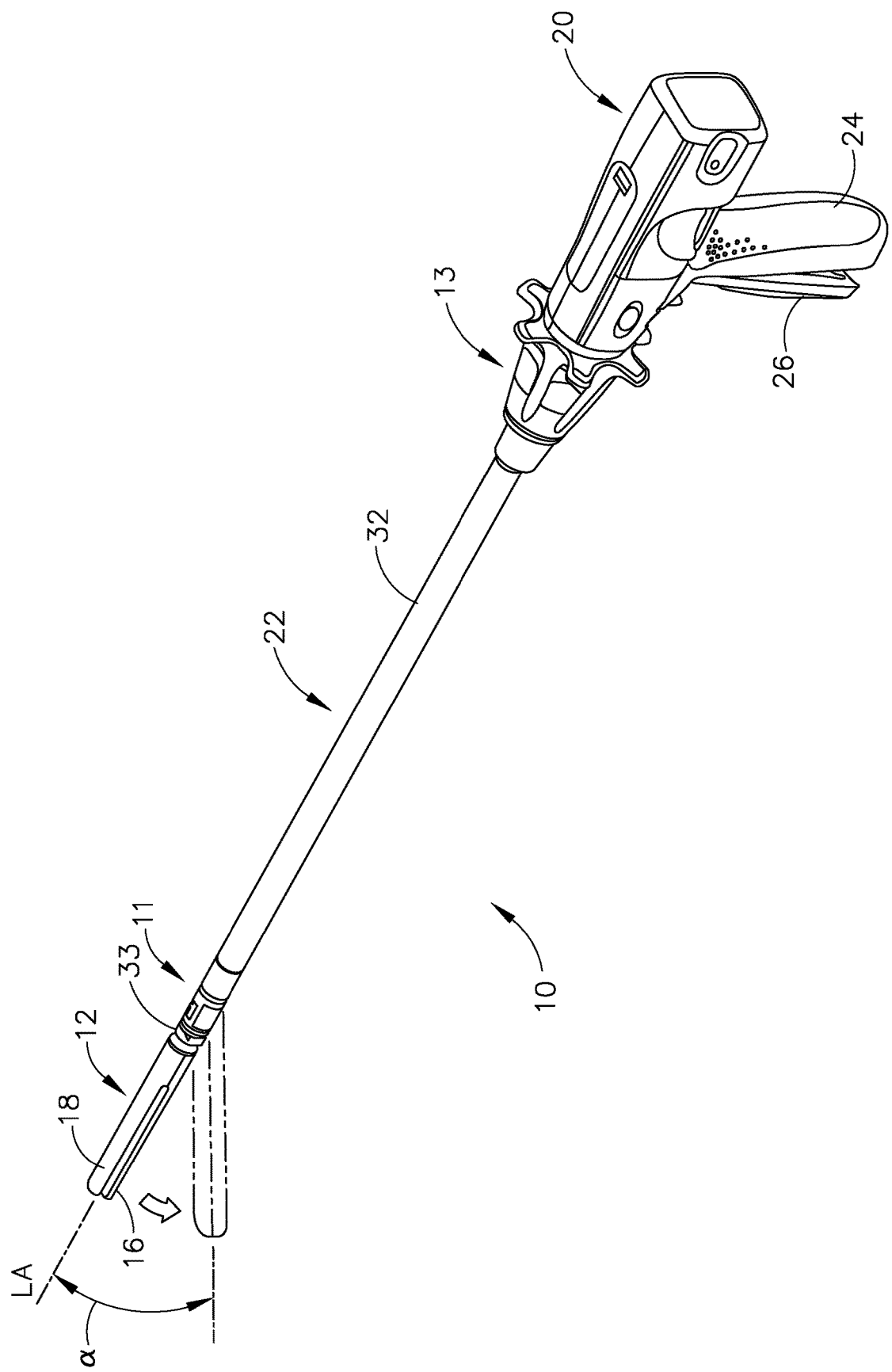
FIG. 1 depicts a perspective view of a first exemplary surgical stapling instrument.
Figure 2:
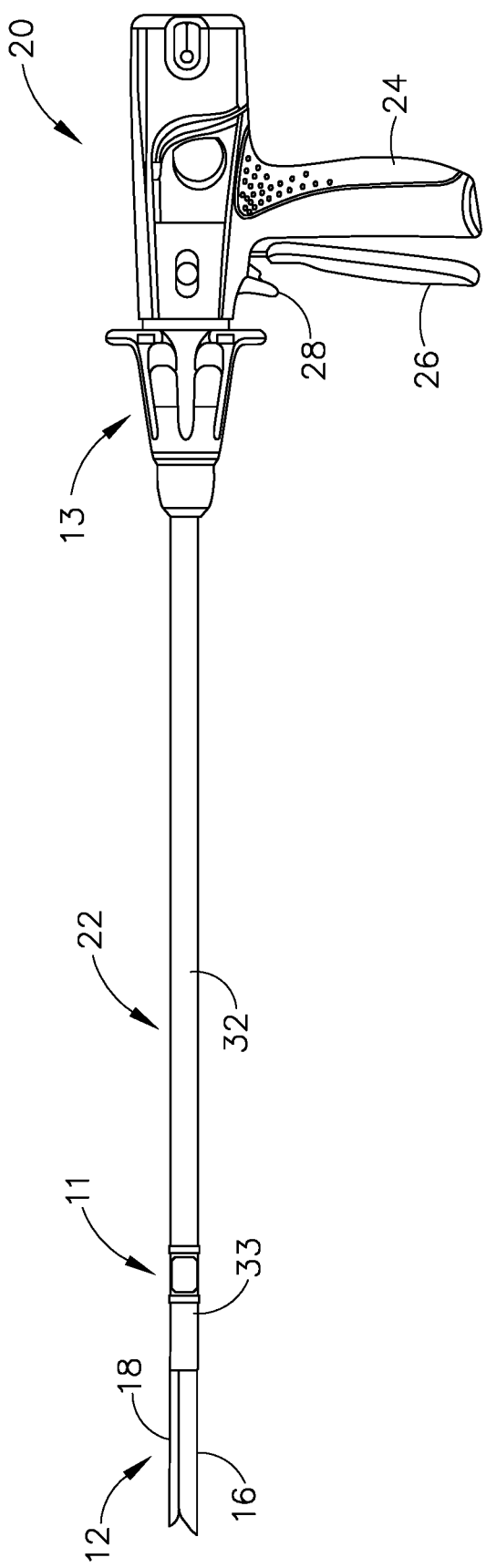
FIG. 2 depicts a side view of the instrument of FIG. 1 with a first exemplary end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. FIRST EXEMPLARY SURGICAL INSTRUMENT HAVING A FIRST EXEMPLARY END EFFECTOR

FIGS. 1-6 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pat. No. 10,092,292, entitled "Staple Forming Features for Surgical Stapling Instrument," issued Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33). Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within an anvil channel (42) of anvil (18). Firing beam cap (44) slidably engages a lower surface of lower jaw (16) by having firing beam (14) extend through lower jaw channel (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
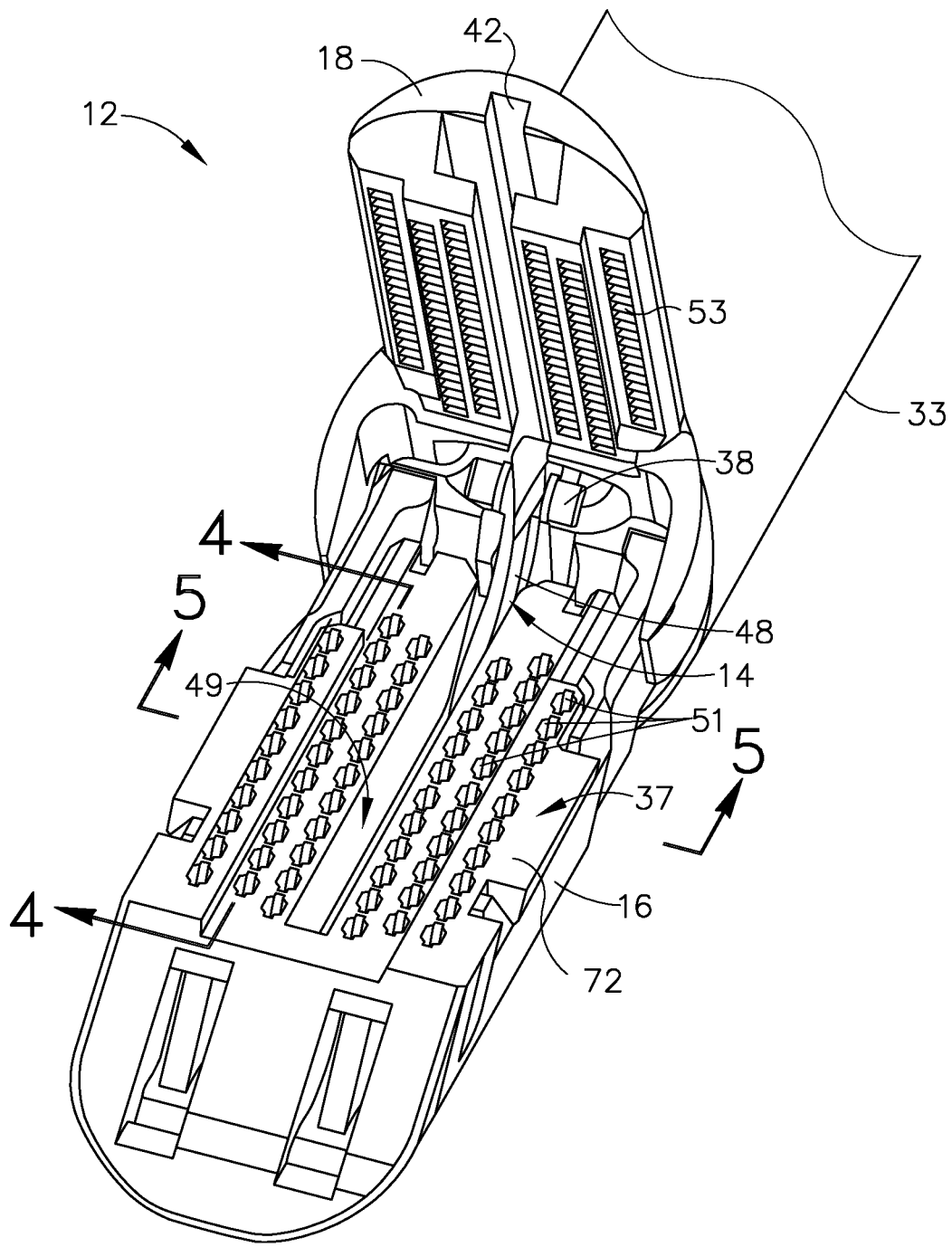
FIG. 3 depicts a perspective view of the end effector of the instrument of FIG. 1 in an open configuration.
Figure 5:
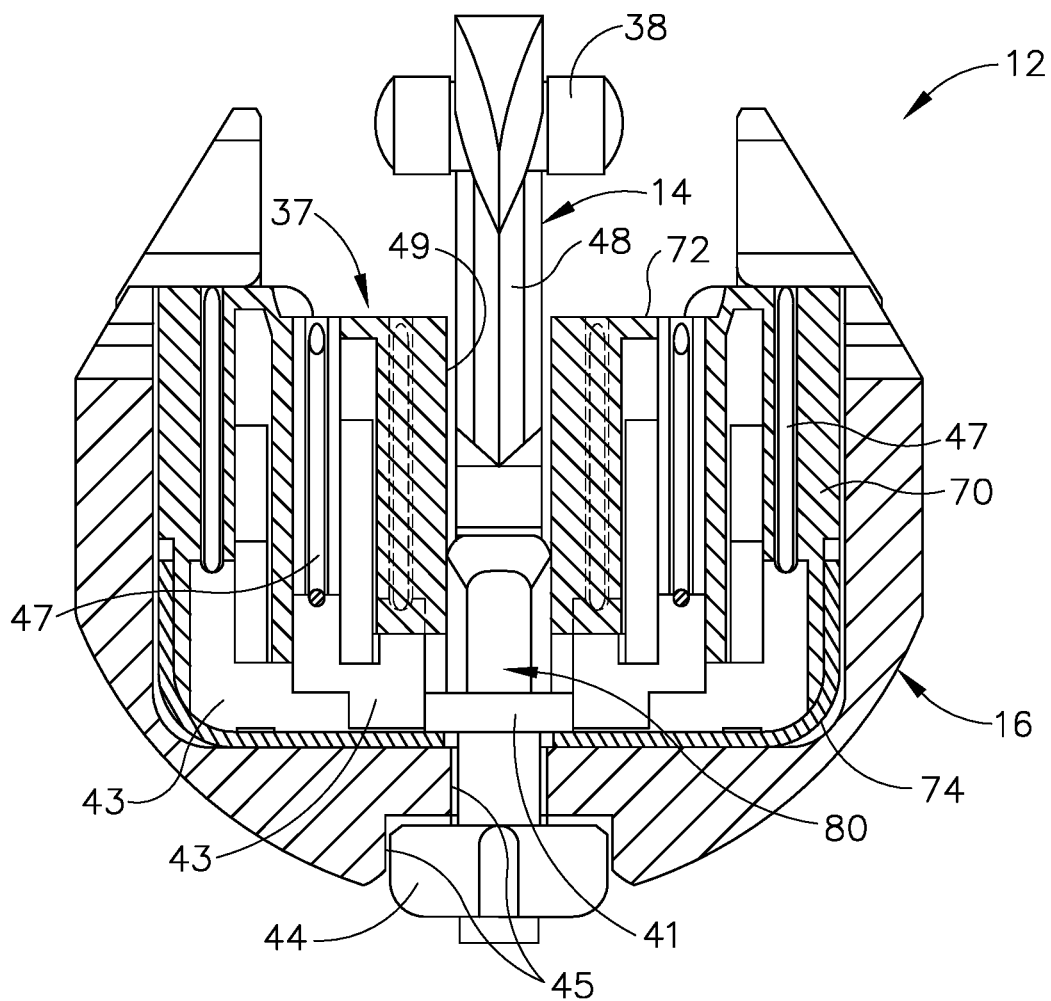
FIG. 5 depicts an end cross-sectional view of the end effector of FIG. 3, taken along line 5-5 of FIG. 3.
Figure 6:
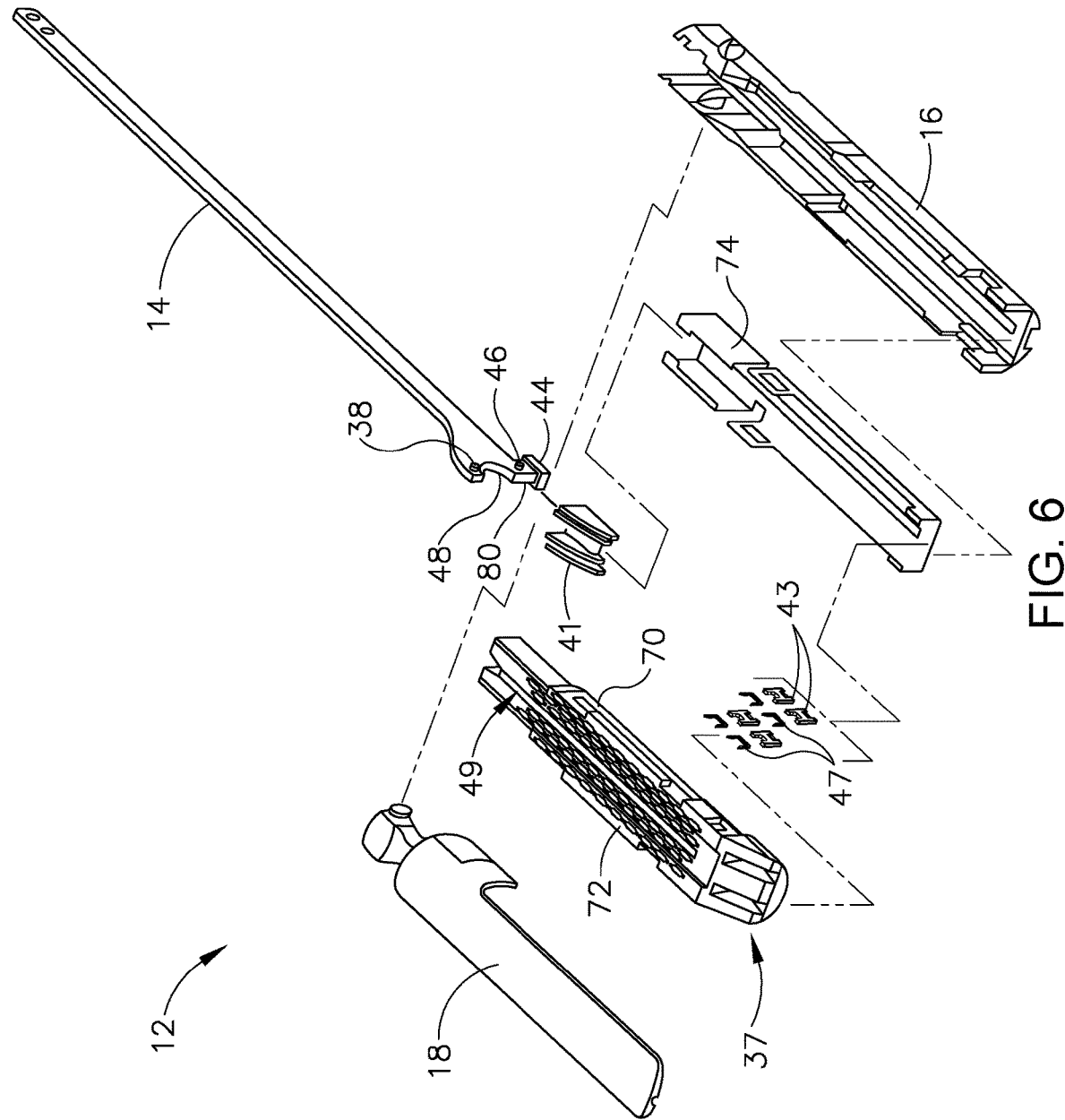
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43)

to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter anvil channel (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY KNIFES AND METHODS OF MANUFACTURE

A. Second Exemplary Instrument

Figure 7:
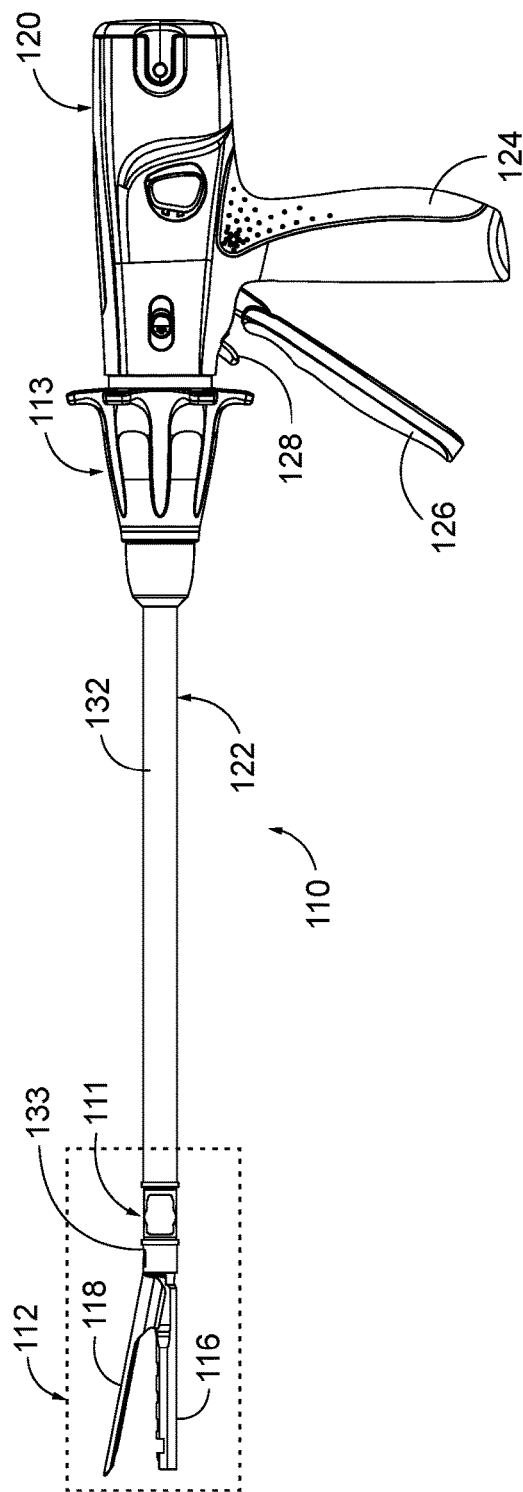
FIG. 7 depicts a perspective view of a second exemplary surgical stapling instrument with a second exemplary end effector.

FIG. 7 shows a perspective view of a second exemplary surgical stapling instrument (110) with a second exemplary end effector (112) that is operable to compress, staple, and cut tissue. Instrument (110) and end effector (112) function similarly to instrument (10) and end effector (12) described above. As shown, instrument (110) includes a body (shown as a handle portion (120)), a shaft (122) extending distally from handle portion (120), with end effector (112) extending distally from shaft (122). Shaft (122) distally terminates in an articulation joint (111), which is coupled with end effector (112).

Similar to instrument (10), handle portion (120) includes a pistol grip (124) and a closure trigger (126). Closure trigger (126) is pivotable toward pistol grip (124) to cause clamping, or closing, of anvil (118) toward lower jaw (116) of end effector (112). Such closing of anvil (118) is provided through a closure tube (132) and a closure ring (133), which both longitudinally translate relative to handle portion (120) in response to pivoting of closure trigger (126) relative to pistol grip (124). Closure tube (132) extends along the length of shaft (122). Closure ring (133) is positioned distal to articulation joint (111). Articulation joint (111) is operable to communicate/transmit longitudinal movement from closure tube (132) to closure ring (133). Handle portion (120) also includes a firing trigger (128). An elongate member (not shown) longitudinally extends through shaft (122) and communicates a longitudinal firing motion from handle portion (120) to a firing beam (114) in response to actuation of firing trigger (128). This distal translation of firing beam (114) causes the stapling and severing of clamped tissue in end effector (112).

Figure 8:
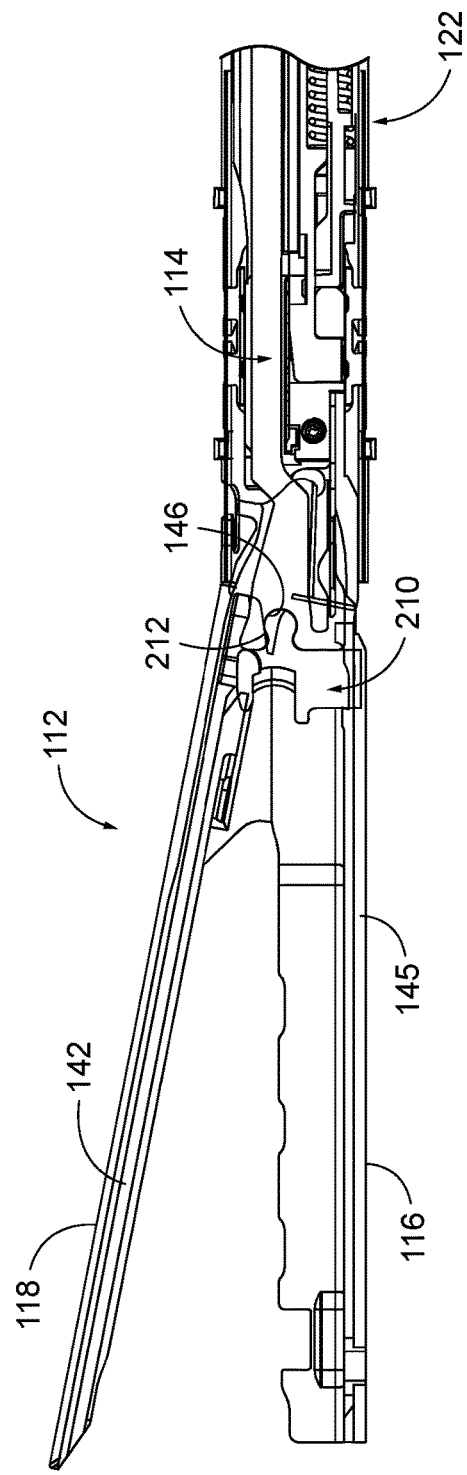
FIG. 8 depicts an enlarged side sectional view of the end effector of FIG. 7.
Figure 9:
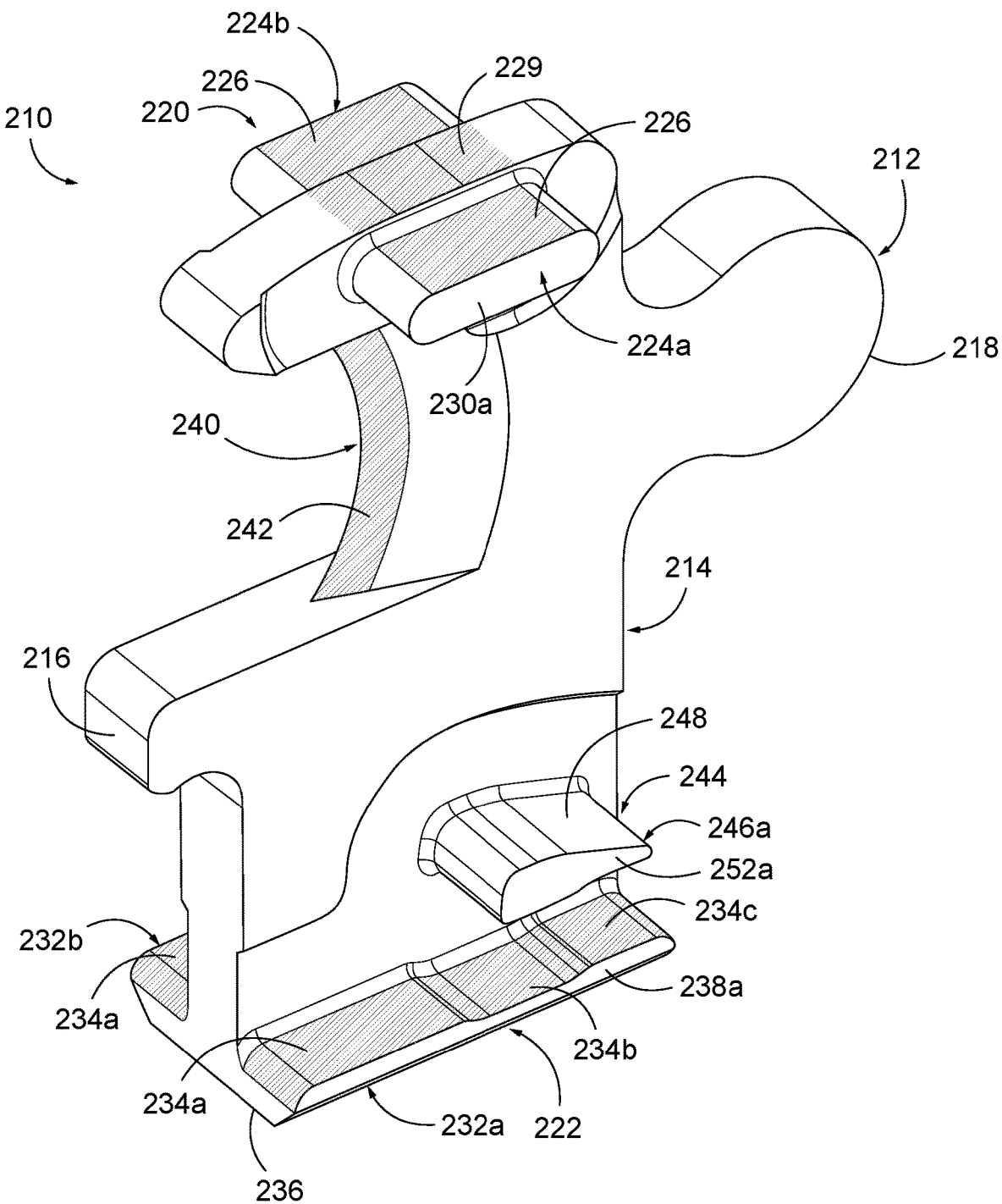
FIG. 9 depicts a top front perspective view of a first exemplary knife of the end effector of FIG. 7.
Figure 10:
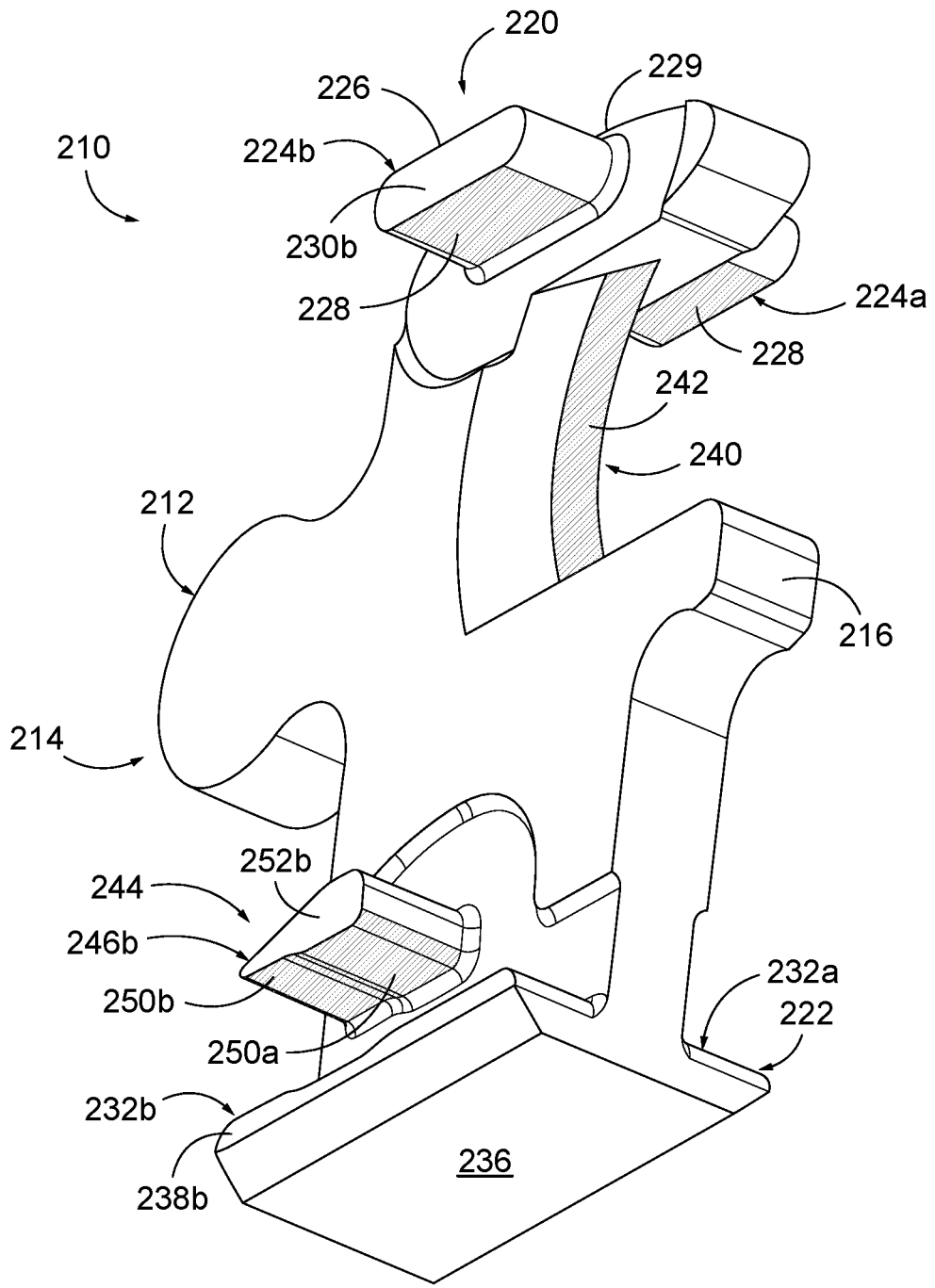
FIG. 10 depicts a bottom front perspective view of knife of FIG. 9.
Figure 11:
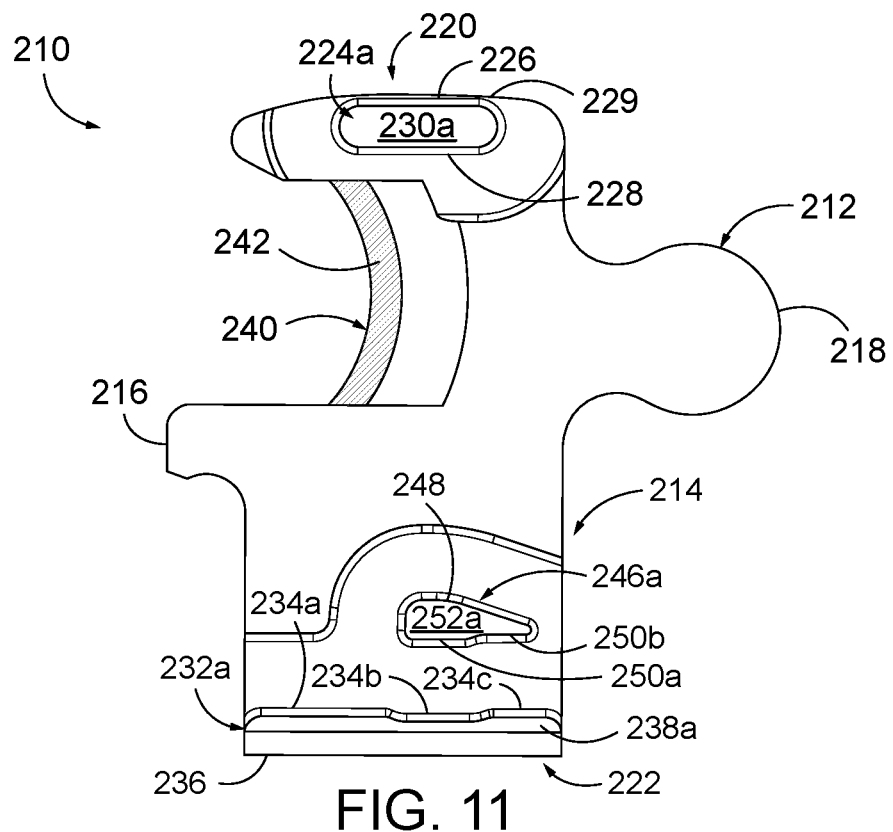
FIG. 11 depicts a left side view of the knife of FIG. 9.
Figure 12:
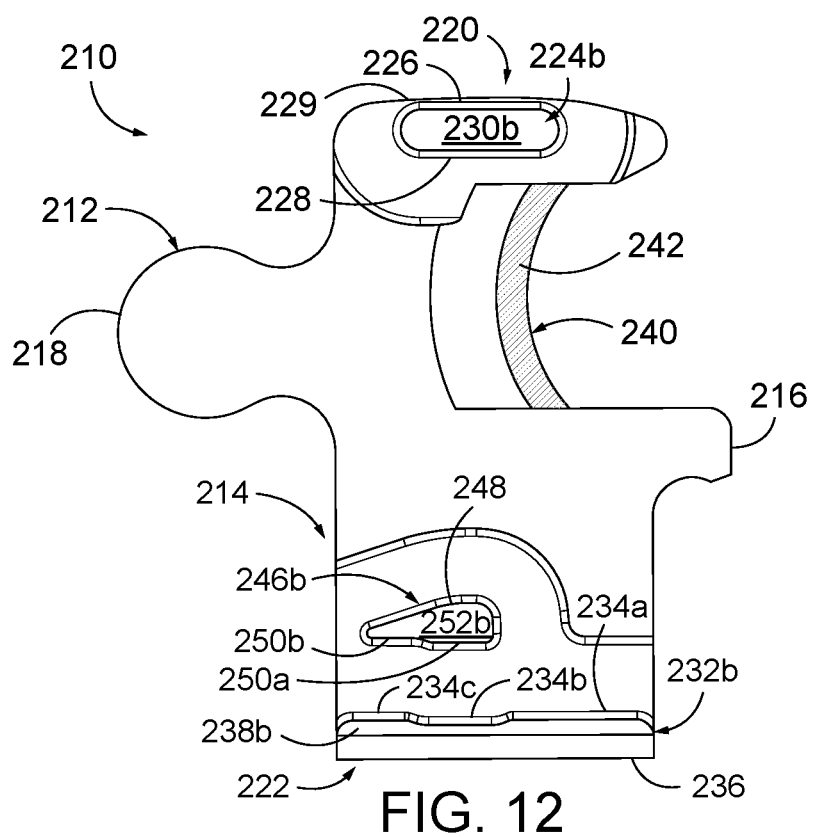
FIG. 12 depicts a right side view of the knife of FIG. 9.

FIG. 8 shows an enlarged side sectional view of end effector (112) of FIG. 7 with a first exemplary knife (210) as will be described in greater detail below with reference to FIGS. 9-12. Lower jaw (116) is configured to receive staple cartridge (37). Lower jaw (116) includes a lower jaw channel (145), similar to lower jaw channel (45), that is configured to receive a portion of knife (210). Likewise, anvil (118) includes an anvil channel (142) similar to anvil channel (42). As shown in FIG. 8, instead of using a single firing beam (14) as shown in FIG. 6, firing beam (14) is separated into firing beam (114) and an exemplary knife (210, 310, 410). Firing beam (114) and knife (210, 310, 410) may be coupled together using a variety of different methods including welding and/or mechanical feature(s). As shown, a distal portion of firing beam (114) includes a coupling feature (146) that couples with a proximal coupling feature (212) of knife (210) as shown in greater detail in FIGS. 9-12.

In some conventional manufacturing processes, knife (210) of instrument (110) may be machined from a single solid block of material (e.g. metal). As a result, this machining of knife (210) may be time consuming and expensive, both of which are undesirable. As a result, it is desirable to manufacture knife (210, 310, 410) using a faster, more efficient, and more cost-effective process or system of processes. Conventional machining techniques, being reductive in nature, may also be considered as being inefficient since they may create waste in the material that is removed from the single solid block of material. Additionally, it may be desirable that specific portions and features of knife (210, 310, 410) have tighter tolerances to enhance the performance of instrument (110), while other specific portions and features of knife (210, 310, 410) may have looser tolerances where the precise dimensions are of lesser significance. For example, tighter tolerances may be preferred for surfaces that aid the distal movement of knife (210, 310, 410) in end effector (112) of instrument (110). As such, it is desirable to manufacture knife (210, 310, 410) efficiently, cost effectively, and robustly. Although the present examples of instruments (10, 110) include surgical staplers, it is contemplated that the teachings may be readily applied to knife members for various other kinds of instruments.

B. First Exemplary Knife

FIG. 9-12 show knife (210) as including a body (214) with distal and proximal ends (216, 218). Body (214) of knife (210) includes an anvil pin (220) disposed opposite a channel pin (222). Anvil pin (220) includes outwardly extending flanges (224a-b). Flanges (224a-b) respectively include upper surfaces (226) separated by upper surface (229), a lower surface (228), and lateral side surfaces (230a-b) disposed therebetween. Flanges (224a-b) are configured to interact with anvil channel (42, 142). Flanges (224a-b) function similarly to upper pin (38) of firing beam (14). Like upper pin (38), flanges (224a-b) are positioned and translatable within anvil channel (42, 142) of anvil (18, 118). Similar to anvil pin (220), channel pin (222) includes outwardly extending flanges (232a-b). Flanges (232a-b) include upper surfaces (234a-c), a lower surface (236), and lateral side surfaces (238a-b) disposed therebetween. Flanges (232a-b) function similarly to firing beam cap (44) that slidably engages a lower surface of lower jaw (16) by having firing beam (14) extend through lower jaw channel (45) (shown in FIG. 4B) that is formed through lower jaw (16). Flanges (224a-b, 232a-b) cooperate to maintain end effector (12, 112) in a closed state during actuation of the end effector (12, 112). As shown, upper surface (234b) is recessed relative to upper surfaces (234a, 234c), resulting in a non-planar surface.

As shown in FIGS. 9-12, a cutting edge (240) is disposed adjacent distal end (216) of knife (210) and opposite coupling feature (212). Cutting edge (240) is formed by the converging distal termination of opposing cutting surfaces (242). Knife (210) also includes a middle flange (244). Middle flange (244) functions similar to middle pins (46) which slidingly engages a top surface of lower jaw (16), cooperating with firing beam cap (44). Middle flange (244) includes outwardly extending flanges (246a-b) that are shown as being generally shaped as airfoils. Flanges (246a-b) include an upper surface (248), a lower surface (250a-b), and lateral side surfaces (252a-b) disposed therebetween.

As shown in FIGS. 9-12 using shading (hatching) of specific surfaces, certain feature(s) may be machined after being initially formed. For example, knife (210) may be initially formed using a near net metal injection molding process. Metal injection molding (MIM) refers to any metalworking process where finely-powdered metal is mixed with a binder material to create a feedstock that is subsequently shaped and solidified using molding process (such as injection molding). Metal injection molding allows for high volume, complex parts to be shaped. As will be described in greater detail below, knife (210, 310, 410) and each of its features have a molded shape, certain features of which are subsequently machined to a machined shape. Machined features may have a finer surface finish than portions of knife (210, 310, 410) that have not been machined.

Such feature(s) being machined after being formed may include one or more of cutting edge (240), upper surface (229) of anvil pin (220), upper and lower surfaces (226, 228) of anvil pin (220), lower surface (250a-b) of middle flange (244), and upper surface (234) of channel pin (222). Machining these features may provide many benefits. For example, upper and lower surfaces (226, 228) may be machined to improve the dimensional tolerances of the near net metal injection molding process. Improved dimensional tolerances of certain surfaces may improve the sliding interface between components moving relative to one another. Improving the sliding interface may reduce the wear associated with upper and lower surfaces (226, 228) of anvil pin (220) slidably interacting with anvil (18, 118). Similarly, upper surface (234a-c) may be machined to reduce the wear associated with slidably interacting with lower jaw channel (145) of lower jaw (116). Opposing cutting surfaces (242) may be machined after being formed using a near net metal injection molding process to increase relative sharpness, which may reduce a cutting force through the tissue. Machining opposing cutting surfaces (242) may specifically include grinding opposing cutting surfaces (242). It is also envisioned that other features including other surfaces may also be machined.

C. Second Exemplary Knife

Figure 13:
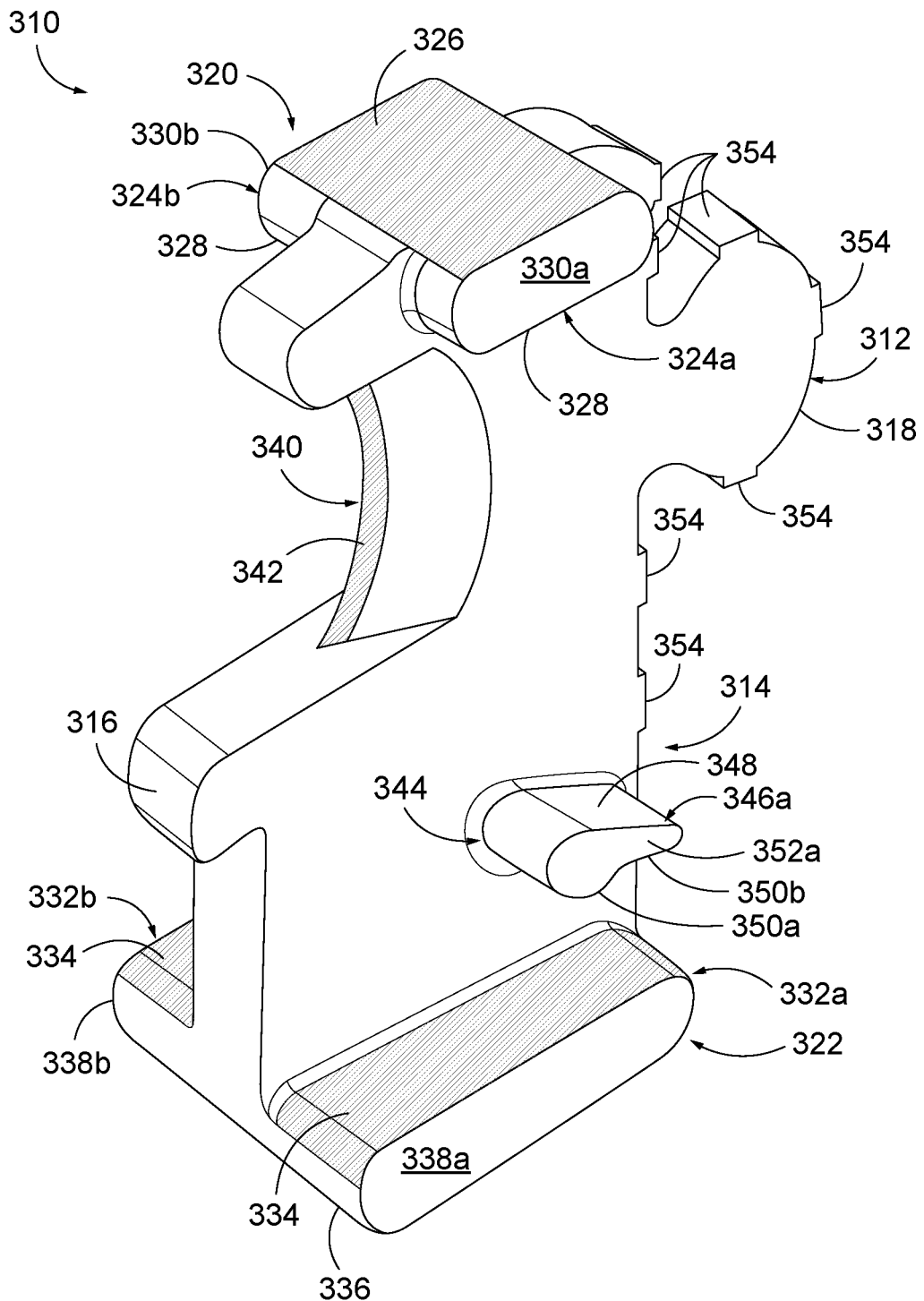
FIG. 13 depicts a top front perspective view of a second exemplary knife that may be incorporated into the end effector of FIG. 7.

FIG. 13 shows a top front perspective view of a second exemplary knife (310) that may be used in end effector (112) in place of knife (210). Knife (310) includes a body (314) with distal and proximal ends (316, 318). Body (314) includes an anvil pin (320) disposed opposite a channel pin (322). Anvil pin (320) includes outwardly extending flanges (324a-b). Flanges (324a-b) include an upper surface (326), a lower surface (328), and lateral side surfaces (330a-b) disposed therebetween. Flanges (324a-b) function similarly to upper pin (38) of firing beam (14) and flanges (224a-b) of knife (210). Like upper pin (38), flanges (324a-b) are positioned and translatable within anvil channel (42, 142) of anvil (18, 118). Similarly, channel pin (322) includes outwardly extending flanges (332a-b). Flanges (332a-b) include an upper surface (334), a lower surface (336), and lateral side surfaces (338a-b) disposed therebetween. Flanges (332a-b) function similarly to firing beam cap (44) and flanges (232a-b) of knife (210). Flanges (324a-b, 332a-b) cooperate to maintain end effector (12, 112) in a closed state during actuation of end effector (12, 112).

Additionally, as shown in FIG. 13, a cutting edge (340) is disposed adjacent distal end (316) of knife (310) and opposite coupling feature (312). Cutting edge (340) is formed by the converging distal termination of opposing cutting surfaces (342). Knife (310) also includes a middle flange (344). Middle flange (344) includes outwardly extending flanges, with outwardly extending flange (346a) being shown and another outwardly extending flange being hidden from view. Flange (346a) includes an upper surface (348), a lower surface (350a-b), and lateral side surface (352a) disposed therebetween. Knife (310) also includes proximal aligning features (354), which are shown as tab shaped projections in the present example. Proximal aligning features (354) may be configured to engage firing beam (14, 114) of surgical instrument (10, 110). While seven proximal aligning features (354) are shown, more or less aligning features of various shapes and sizes are also envisioned. Additionally, the spacing between adjacent proximal aligning features (354) may vary.

Figure 14A:
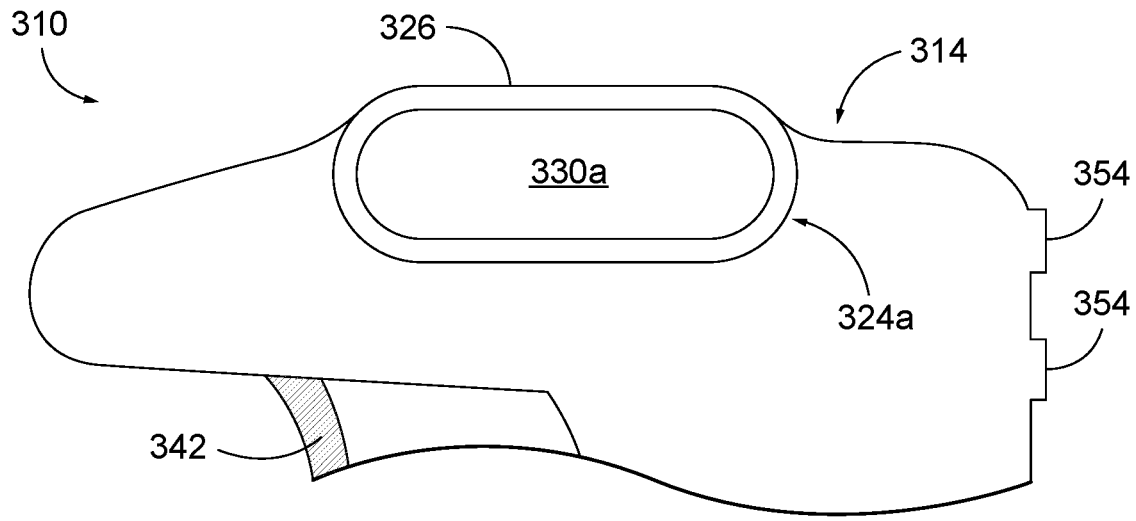
FIG. 14A depicts an enlarged view of the anvil pin of the knife of FIG. 13 prior to being machined.
Figure 14B:
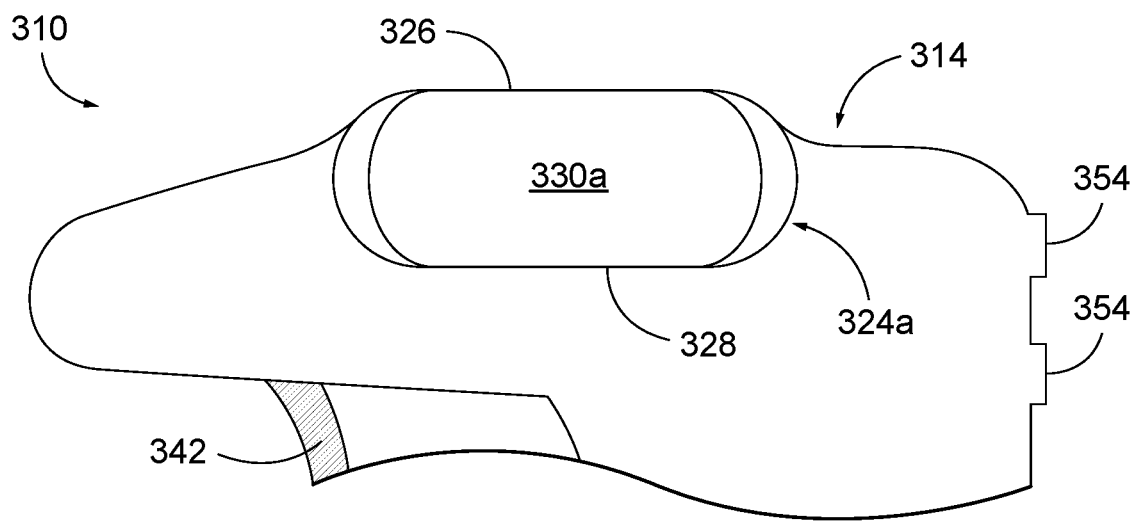
FIG. 14B depicts an enlarged view of the anvil pin of the knife of FIG. 13 after being machined.

As shown in FIGS. 13-14B using shading (hatching) of specific surfaces, certain feature(s) may be machined after being formed. Such feature(s) may include one or more of opposing cutting surfaces (342) of cutting edge (340), upper and lower surfaces (326, 328) of anvil pin (320), lower surface (350a-b) of middle flange (344), and upper surface (334) of channel pin (322). For example, upper and lower surfaces (326, 328) may be machined to reduce wear while slidably interacting with anvil (18, 118). Similarly, upper surface (334) of channel pin (322) may be machined to reduce the wear associated with slidably interacting with lower jaw channel (145) of lower jaw (116). Also, opposing cutting surfaces (342) may be machined (e.g. ground using a grinder) to increase the sharpness of cutting surfaces (342) which reduces the cutting force through the tissue. It is also envisioned that other features and surfaces may also be machined.

FIG. 14A shows an enlarged view of anvil pin (320) of knife (310) of FIG. 13 prior to machining but after being formed using a near net metal injection molding process. FIG. 14B shows an enlarged view of anvil pin (320) of knife (310) after machining. As shown 14A, upper and lower surfaces (326, 328) are machined to obtain the upper and lower surfaces (326, 328) in FIG. 14B. Machining removes material from the feature, such that the dimensions of the molded shape are greater than dimensions of machined shape of the specific feature. For example, these reduced dimensions may be seen in FIGS. 14A-14B showing the molded and subsequently machined upper and lower surfaces (326, 328) of anvil pin (320) of knife (310).

D. Third Exemplary Knife

Figure 15:
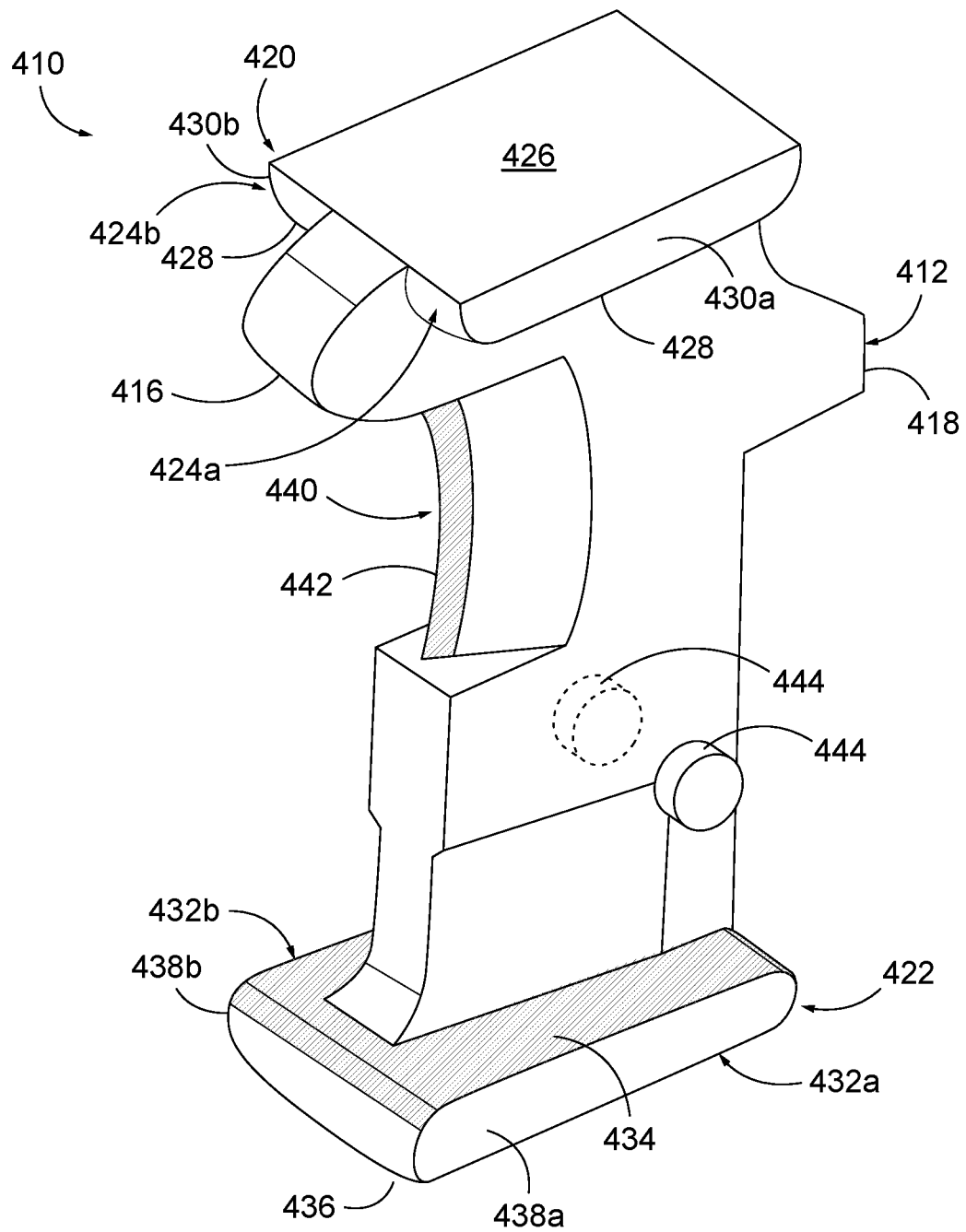
FIG. 15 depicts a top front perspective view of a third exemplary knife that may be incorporated into the end effector of FIG. 7.

FIG. 15 shows a top front perspective view of a third exemplary knife (410) that may be used in end effector (112) in place of knife (210, 310). Knife (410) includes a body (414) with distal and proximal ends (416, 418). Body (414) includes an anvil pin (420) disposed opposite a channel pin (422). Anvil pin (420) includes outwardly extending flanges (424a-b). Flanges (424a-b) include an upper surface (426), a lower surface (428), and lateral side surfaces (430a-b) disposed therebetween. Flanges (424a-b) function similarly to upper pin (38) of firing beam (14) and flanges (224a-b, 324a-b) of knife (210, 310). Like upper pin (38), flanges (324a-b) are positioned and translatable within anvil channel (42, 142) of anvil (18, 118). Similarly, channel pin (422) includes outwardly extending flanges (432a-b). Flanges (432a-b) include an upper surface (434), a lower surface (436), and lateral side surfaces (438a-b) disposed therebetween. Flanges (432a-b) function similarly to firing beam cap (44) and flanges (232a-b, 332a-b)) of knife (210, 310). Flanges (424a-b, 432a-b) cooperate to maintain end effector (12, 112) in a closed state during actuation of end effector (12, 112).

Additionally, as shown in FIG. 15, a cutting edge (440) is disposed adjacent distal end (416) of knife (410) and opposite coupling feature (412). Cutting edge (440) is formed by the converging distal termination of opposing cutting surfaces (442). Knife (410) also includes a middle pin (444) adjacent proximal end (418) of knife (410). Middle pin (444) is functionally equivalent to middle pin (46). Similar to middle pin (46) that slidingly engages a top surface of lower jaw (16) cooperating with firing beam cap (44) described above with reference to FIGS. 1-6, middle pin (444) is configured to slidingly engage a top surface of lower jaw (16, 116), cooperating with flanges (424a-b).

As shown in FIG. 15 with regard to knife (410), certain feature(s) may be machined after being formed. Such feature(s) may include one or more of opposing cutting surfaces (442) of cutting edge (440), lower surface (428) of anvil pin (420), and upper surface (434) of channel pin (422). For example, upper and lower surfaces (426, 428) may be machined to reduce the wear associated with slidably interacting with anvil (18, 118). Similarly, upper surface (434) of channel pin (422) may be machined to improve the respective tolerances which may reduce the associated wear while slidably interacting with lower jaw channel (145) of lower jaw (116). Opposing cutting surfaces (442) may be machined to reduce a cutting force through the tissue. It is also envisioned that other features and surfaces may also be machined.

E. Exemplary Method of Manufacturing

Figure 16:
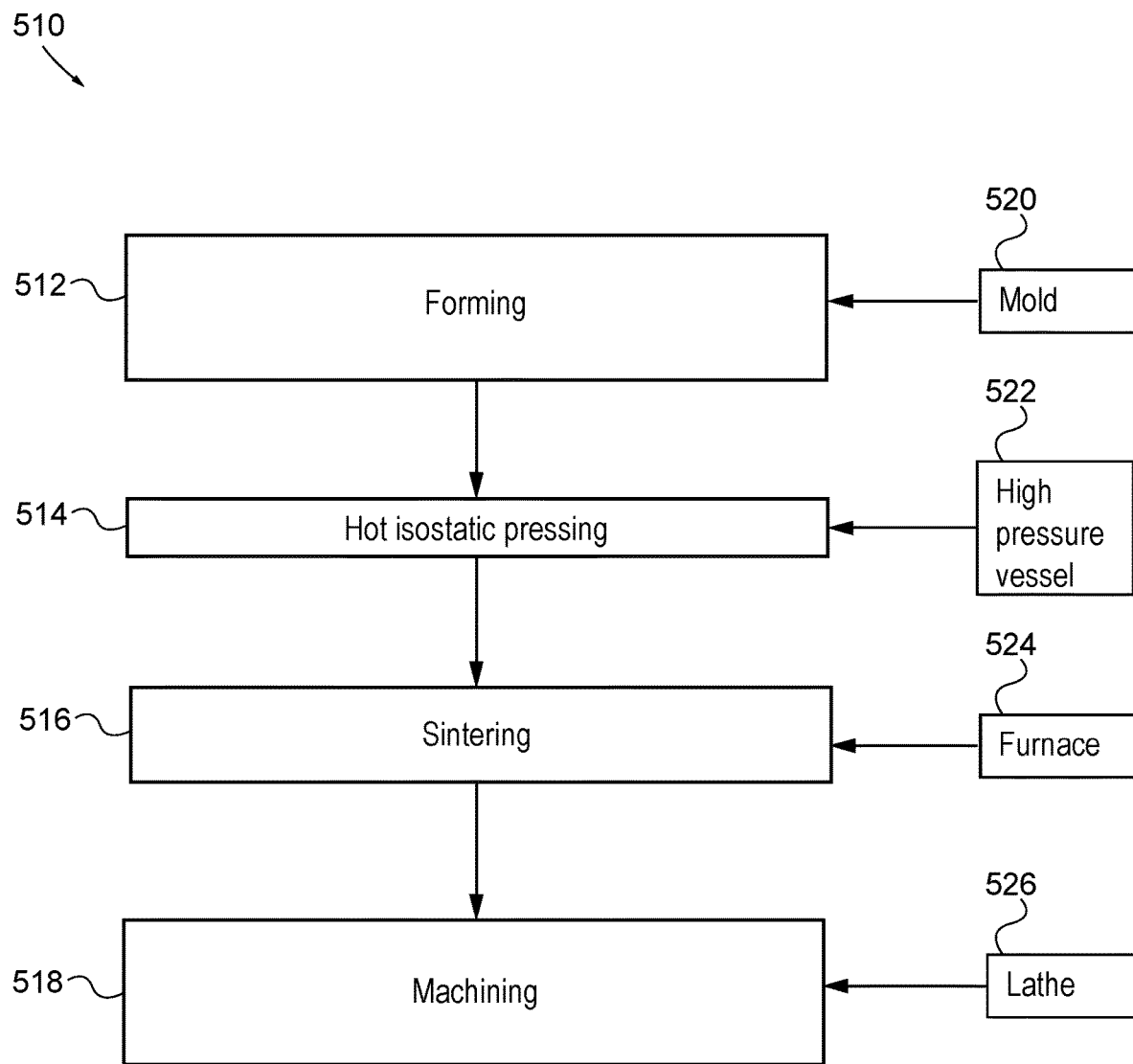
FIG. 16 depicts an exemplary method of manufacturing a knife that may be incorporated into the end effector of FIG. 7.

FIG. 16 shows an exemplary method (510) of manufacturing knife (210, 310, 410) of end effector (12, 112) of surgical instrument (10, 110) that includes steps (512, 514, 516, 518). As shown, at step (512), method (510) includes forming knife (210, 310, 410) using metal injection molding using a mold (520). Knife (210, 310, 410) and each of its features have a molded shape. Instead of using metal injection molding, knife (210, 310, 410) may be formed using selective laser melting, or direct metal laser sintering, or any other suitable additive manufacturing process.

At step (514), method (510) includes hot isostatic pressing knife (210, 310, 410) using a high-pressure vessel (522). Hot isostatic pressing (HIP) is a manufacturing process that is used to reduce the porosity of metals and increase the density of many ceramic materials. Hot isostatic pressing may result in one or more of densification of powdered components, elimination of internal porosity, improvement of mechanical properties (such as increased resistance to fatigue and temperature extremes, higher resistance to impact, wear and abrasion, and improved ductility), more efficient production (tighter tolerances, reduction in machining, reduction in scrap). Hot isostatic pressing may be used on metal components, ceramic components, and/or composite components. For example, knife (210, 310, 410) may be placed into high-pressure vessel (522) and subjected to high pressurized gases and/or high temperatures. While the hot isostatic pressing is shown in FIG. 16 as occurring at a time prior to machining, it is also envisioned that the hot isostatic pressing may occur at a time after machining. In other words, step (514) may occur before or after step (518). It is desirable to selectively use hot isostatic pressing on particular structural features of knife (210, 310, 410).

At step (516), method (510) includes sintering knife (210, 310, 410) after hot isostatic pressing knife (210, 310, 410). Prior to sintering, knife (210, 310, 410) is considered to be in a "green state." Sintering may be performed by inserting knife (210, 310, 410) into a furnace (524).

At step (518), method (510) includes machining feature(s) of knife (210, 310, 410) to have a machined shape. It is desirable to machine only specific feature(s) of knife (210, 310, 410) without machining the entire knife (210, 310, 410). The feature(s) may include a plurality of drive surfaces and cutting edge (240, 340, 440) of knife (210, 310, 410). More specifically, the feature(s) may include cutting edge (240, 340, 440), anvil pin (220, 320, 420), middle flange (244, 344), and channel pin (222, 322, 422) of knife (210, 310, 410). More specifically, the surfaces of the feature(s) may include opposing cutting surfaces (242, 342, 442) of cutting edge (240, 340, 440), upper surface (229) of anvil pin (220), upper surface (226, 326, 426) of channel pin (222, 322, 422), lower surface (228, 328, 428) of anvil pin (220, 320, 420), and bottom surface (250a-b, 350a-b) of middle flange (244, 344). It may be desirable to machine at least two of these surfaces, at least three of these surfaces, at least four of these surfaces, or at least each of these surfaces. If two or more features are imparted, the features may be refined simultaneously or sequentially.

Machining removes material from the feature(s), such that the dimensions of the molded or otherwise pre-machined shape are greater than dimensions of machined shape for the assessed feature. For example, the dimension reductions may be seen in comparing FIG. 14A showing the molded anvil pin (320) of knife (310) and FIG. 14B showing the subsequently machined anvil pin (320). Machining specific features, and specific surfaces of specific features, imparts tight tolerances where expressly desired. For example, tight tolerances may be preferred to minimize friction and associated wear of anvil pin (220, 320, 420) and channel pin (222, 322, 422). Step (518) may be performed using a variety of machining tools, for example, using a lathe (526), which may be manually operated or automated. Machining is desired to broadly encompass turning operation(s), milling operation(s), drilling operations(s), and other miscellaneous machining operations. For example, machining may include grinding opposing cutting surfaces (242, 342, 442) of cutting edge (240, 340, 440).

Machining specific features may identify material voids adjacent an outer surface of the feature that are present after hot isostatic pressing features of knife (210, 310, 410). Additionally, this secondary clean-up machining allows for initial molded geometries having better mold flow characteristics for the metal injection molding process. These machining operations may leave indication marks on the connected side walls that show where machining was used and the amount of material removed. Metal injection molding knife (210, 310, 410), sintering, and subsequently machining at least lower surface (228, 328, 428) of anvil pin (220, 320, 420) and upper surface (226, 326, 426) of channel pin (222, 322, 422), strengthens anvil pin (220, 320, 420) and channel pin (222, 322, 422). Improved anvil pin (220, 320, 420) and channel pin (222, 322, 422) characteristics reduce the requisite force to advance knife (210, 310, 410) under loading. As such, using a near net metal injection molding process and subsequent machining provides knife (210, 310, 410) with higher performance machined features on the same distal component. Additionally, method (510) provides a superior surface finish than metal injection molding is capable of alone.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor-in interest to the inventors. If any claims are presented in this application or in subsequent filings related to this application that include additional features beyond those referred to below, those additional features shall not be presumed to have been added for any reason relating to patentability.

Example 1

A method of manufacturing a knife of an end effector of a surgical instrument, the method comprising: (a) forming the knife using metal injection molding, wherein the knife has at least one feature having a molded shape; (b) machining the at least one feature of the knife to have a machined shape without machining the entire knife; and (c) incorporating the knife into the end effector of the surgical instrument.

Example 2

The method of Example 1, wherein the machining removes material from the at least one feature, such that the dimensions of the molded shape are greater than the dimensions of the machined shape of the at least one feature.

Example 3

The method of Examples 1 or 2, further comprising: hot isostatic pressing the knife before or after machining the at least one feature.

Example 4

The method of Example 3, wherein hot isostatic pressing occurs before machining the at least one feature.

Example 5

The method of Examples 3 or 4, further comprising: sintering the knife after hot isostatic pressing the knife and before machining the at least one feature of the knife.

Example 6

The method of any one or more of Examples 1 through 5, wherein machining the at least one feature further comprises machining a plurality of drive surfaces and cutting surfaces of the knife.

Example 7

The method of any one or more of Examples 3 through 6, wherein machining the at least one feature identifies material voids adjacent an outer surface of the at least one feature present after the hot isostatic pressing of the knife.

Example 8

The method of any one or more of Examples 1 through 5, wherein machining the at least one feature further comprises machining at least a portion of each of a cutting edge, an anvil pin, a middle flange, and a channel pin of the knife.

Example 9

The method of any one or more of Examples 1 through 5, wherein machining the at least one feature further comprises machining at least each of a cutting edge, a lower surface of an anvil pin, and an upper surface of a channel pin of the knife.

Example 10

The method of Example 9, wherein the upper surface of the channel pin is non-planar.

Example 11

The method of any one or more of Examples 1 through 5, wherein machining the at least one feature further comprises machining upper and lower surfaces of an anvil pin of the knife.

Example 12

The method of any one or more of Examples 1 through 5, wherein machining the at least one feature further comprises machining at least three of a cutting edge, an upper surface of the anvil pin, a lower surface of the anvil pin, a lower surface of the middle flange, or an upper surface of a channel pin of the knife.

Example 13

The method of any one or more of Examples 1 through 5, wherein machining the at least one feature further comprises machining at least each of a cutting edge, an upper surface of the anvil pin, a lower surface of the anvil pin, a lower surface of the middle flange, and an upper surface of a channel pin of the knife.

Example 14

The method of any one or more of Examples 1 through 13, wherein machining the at least one feature produces a finer surface finish than a portion of the knife that has not been machined.

Example 15

The method of any one or more of Examples 1 through 14, wherein the knife further comprises a plurality of proximal aligning features configured to engage a firing rod of the surgical instrument.

Example 16

A method of manufacturing a knife of an end effector of a surgical instrument, the method comprising: (a) forming the knife using metal injection molding, wherein the knife has at least one feature having a molded shape and a first surface finish; (b) hot isostatic pressing the knife; (c) machining the at least one feature of the knife to have a machined shape and a second surface finish without machining the entire knife, wherein the second surface finish is finer than the first surface finish; and (d) incorporating the knife into the end effector of the surgical instrument.

Example 17

The method of Example 16, wherein machining the at least one feature further comprises machining at least each of a cutting edge, a lower surface of an anvil pin, and an upper surface of a channel pin.

Example 18

The method of Example 16, wherein machining the at least one feature includes grinding a cutting edge of the knife.

Example 19

An instrument, comprising: (a) a handle assembly; (b) a shaft extending from the handle assembly; and (c) an end effector in communication with the shaft, wherein the end effector is operable to compress, staple, and cut tissue, wherein the end effector comprises: (i) a first jaw including a channel and configured to receive a staple cartridge, (ii) a second jaw including an anvil, and (iii) a knife, wherein the knife comprises: (A) a cutting edge including first and second opposing sides, wherein the first and second opposing sides are machined with a configuration to reduce a cutting force through the tissue, (B) an anvil pin including upper and lower surfaces, wherein at least the lower surface is machined with a configuration to reduce wear associated with slidably interacting with the anvil, and (C) a channel pin that includes upper and lower surfaces, wherein at least the upper surface is machined with a configuration to reduce wear associated with slidably interacting with the channel.

Example 20

The instrument of Example 19, wherein the knife further includes a middle flange that includes upper and lower surfaces, wherein the lower surface of the middle flange is machined, wherein both the upper and lower surfaces are machined to reduce the wear associated with slidably interacting with the channel.

Example 21

An instrument, comprising: (a) a handle assembly; (b) a shaft extending from the handle assembly; and (c) an end effector in communication with the shaft, wherein the end effector is operable to compress, staple, and cut tissue, wherein the end effector comprises: (i) a first jaw including a channel and configured to receive a staple cartridge, (ii) a second jaw including an anvil, and (iii) a knife, wherein the knife comprises: (A) a body formed using metal injection molding and having a first surface finish, (B) at least one feature formed in the body and having a molded shape, wherein the at least one feature of the knife is subsequently machined to have a machined shape with a second surface finish without machining the entire knife, wherein the second surface finish is finer than the first surface finish.

Example 22

The instrument of any one or more of Examples 19 through 21, wherein the dimensions of the molded shape are greater than the dimensions of the machined shape of the at least one feature.

Example 23

The instrument of any one or more of Examples 19 through 22, wherein the knife undergoes hot isostatic pressing before or after machining the at least one feature.

Example 24

The instrument of Example 23, wherein the knife is sintered after hot isostatic pressing the knife and before the at least one feature of the knife is machined.

Example 25

The instrument of any one or more of Examples 21 through 24, wherein the at least one feature comprises a plurality of drive surfaces and cutting surfaces of the knife.

Example 26

The instrument of any one or more of Examples 21 through 25, wherein the at least one feature is machined to identify material voids adjacent an outer surface of the at least one feature present after hot isostatic pressing the knife.

Example 27

The instrument of any one or more of Examples 19 through 26, wherein the at least one feature further comprises at least a portion of each of a cutting edge, an anvil pin, a middle flange, and a channel pin of the knife.

Example 28

The instrument of any one or more of Examples 21 through 24, wherein the at least one feature further comprises at least each of a cutting edge, a lower surface of an anvil pin, and an upper surface of a channel pin of the knife.

Example 29

The instrument of any one or more of Examples 21 through 26, wherein the at least one feature further comprises upper and lower surfaces of an anvil pin of the knife.

Example 30

The instrument of any one or more of Examples 21 through 24, wherein the at least one feature further comprises at least three of a cutting edge, an upper surface of the anvil pin, a lower surface of the anvil pin, a lower surface of the middle flange, or an upper surface of a channel pin of the knife.

Example 32

The instrument of any one or more of Examples 21 through 24, wherein the at least one feature further comprises at least each of a cutting edge, an upper surface of the anvil pin, a lower surface of the anvil pin, a lower surface of the middle flange, and an upper surface of a channel pin of the knife.

Example 33

The instrument of any one or more of Examples 21 through 32, wherein the at least one feature has a finer surface texture after being machined than a portion of the knife that has not been machined.

Example 34

The instrument of any one or more of Examples 19 through 33, wherein the knife further comprises a plurality of proximal aligning features configured to engage a firing rod of the surgical instrument.

IV. MISCELLANEOUS

It should be understood that any one or more of the teachings, expressions, embodiments, examples, etc. described herein may be combined with any one or more of the other teachings, expressions, embodiments, examples, etc. that are described herein.

The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc. of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a knife of an end effector of a surgical instrument, wherein the knife extends along a longitudinal axis, the method comprising:
   (a) metal injection molding the knife to include at least first and second pins that extend laterally away from the longitudinal axis and a middle portion that extends along the longitudinal axis and includes a cutting edge; and
   (b) machining at least a portion of the first pin of the knife and machining a recess into a portion of the second pin after metal injection molding the first pin, the second pin, and the middle portion, wherein the second pin includes an upper surface that faces the first pin and includes the recess, wherein the first pin is configured to be slidably received within a longitudinally extending recess of a first jaw of the end effector and the second pin is configured to be slidably received within a longitudinally extending recess of a second jaw of the end effector, wherein the first and second pins are configured to be slidably received by the respective first and second jaws simultaneously.

2. The method of claim 1, further comprising incorporating the knife into the end effector of the surgical instrument so that the first pin is movable within the longitudinally extending recess of the first jaw of the end effector and the second pin is movable within the longitudinally extending recess of the second jaw of the end effector.

3. The method of claim 1, wherein metal injection molding the knife to include the first pin further comprises metal injection molding the knife to include opposing first and second flanges of the first pin.

4. The method of claim 3, wherein the opposing first and second flanges of the first pin each include upper and lower surfaces, wherein machining at least the portion of the first pin further comprises machining at least three of the upper surface of the first flange, the lower surface of the first flange, the upper surface of the second flange, or the lower surface of the second flange.

5. The method of claim 1, wherein machining the portion of the first pin includes removing an outer surface of the first pin, the outer surface being adjacent to a material void on the portion of the first pin, wherein the machining step produces a finer surface finish than a portion of the knife that has not been machined.

6. The method of claim 1, wherein the machining step is performed without machining the entire knife.

7. The method of claim 1, further comprising:
  (a) hot isostatic pressing the knife before or after machining the first pin; and
  (b) sintering the knife by placing the knife into a furnace after hot isostatic pressing the knife and before machining the portion of the first pin.

8. The method of claim 1, wherein metal injection molding the knife is performed using a single metal injection molding process.

9. The method of claim 1, wherein metal injection molding the knife to include the second pin further comprises metal injection molding the knife to include opposing first and second flanges of the second pin.

10. The method of claim 1, wherein the first pin includes upper and lower surfaces, wherein the second pin further includes a lower surface, wherein the machining step further comprises machining at least three of the upper surface of the first pin, the lower surface of the first pin, the upper surface of the second pin, or the lower surface of the second pin.

11. The method of claim 1, wherein the first pin includes an anvil pin, wherein the first jaw includes an anvil, wherein the second pin includes a channel pin, wherein the second jaw includes a stapling assembly, the method further comprising incorporating the knife into the surgical instrument so that the first pin is movable within a longitudinally extending recess of the anvil and the second pin is movable within a longitudinally extending recess of the stapling assembly.

12. The method of claim 11, wherein metal injection molding further comprises metal injection molding the knife to include a pin or flange that extends laterally away from of the longitudinal axis, wherein the pin or flange is disposed between the first and second pins.

13. The method of claim 12, further comprising incorporating the knife into the surgical instrument so that the pin or flange is movable along a surface of the second jaw of the end effector.

14. The method of claim 12, wherein the machining step further comprises machining at least a portion of the pin or flange.

15. A method of manufacturing a knife of an end effector of a surgical instrument, wherein the knife extends along a longitudinal axis, the method comprising:
  (a) forming the knife using one of metal injection molding, selective laser melting, or direct metal laser sintering so that the knife includes first and second pins that extend laterally away from the longitudinal axis and a middle portion that extends between the first and second pins;
  (b) machining at least a portion of each of the first and second pins of the knife after metal injection molding the knife to include the first and second pins; and
  (c) incorporating the knife into the end effector of the surgical instrument so that the first pin is movable within a longitudinally extending recess of a first jaw of the end effector and the second pin is movable within a longitudinally extending recess of a second jaw of the end effector, wherein the first and second pins are configured to be movably received by the respective first and second jaws simultaneously,
  wherein machining the second pin includes reducing a contact area that slidably engages the second jaw to thereby minimize a sliding friction between the second pin and the second jaw.

16. The method of claim 15, wherein metal injection molding the knife is performed using a single metal injection molding process.

17. The method of claim 15, wherein metal injection molding further comprises metal injection molding the middle portion to include a third pin or flange that extends laterally away from of the longitudinal axis and is disposed between the first and second pins.

18. A method of manufacturing a knife of an end effector of a surgical instrument, wherein the knife extends along a longitudinal axis, the method comprising:
  (a) metal injection molding the knife using a single metal injection molding process to include first, second, and third projections that extend laterally away from the longitudinal axis along respective axes that are offset from one another and are non-parallel to the longitudinal axis, wherein the second projection extends distally beyond the first projection and is configured to directly contact a portion of the end effector; and
  (b) incorporating the knife into the end effector of the surgical instrument.

19. The method of claim 18, wherein the end effector includes first and second jaws, wherein incorporating the knife into the end effector of the surgical instrument further comprises incorporating the knife into the end effector of the surgical instrument so that the first projection is movable within a longitudinally extending recess of the first jaw of the end effector, the second projection is movable within a longitudinally extending recess of a second jaw of the end effector, and the third projection is movable along a surface of the second jaw of the end effector.

20. The method of claim 18, further comprising: machining at least a portion of each of the first, second, and third projections of the knife.

\* \* \* \* \*